United States Patent
Tsoi et al.

[11] Patent Number: 5,972,584
[45] Date of Patent: Oct. 26, 1999

[54] AUXILIARY DEVELOPMENT AGENTS PHOTOGRAPHIC MATERIALS INCORPORATING THEM AND THE USE THEREOF

[75] Inventors: Siu C. Tsoi, Watford; Peter J. Twist, Gt. Missenden, both of United Kingdom

[73] Assignee: Eastman Kodak Company, Rochester, N.Y.

[21] Appl. No.: 09/255,925

[22] Filed: Feb. 23, 1999

Related U.S. Application Data

[62] Division of application No. 08/970,640, Nov. 14, 1997.

[30] Foreign Application Priority Data

Nov. 14, 1996 [GB] United Kingdom ............... 9623709

[51] Int. Cl.⁶ ........................................... G03C 5/30
[52] U.S. Cl. ............................. 430/483; 430/480
[58] Field of Search ........................ 430/480, 483

[56] References Cited

U.S. PATENT DOCUMENTS

| | | | |
|---|---|---|---|
| 2,772,282 | 11/1956 | Allen et al. | 430/469 |
| 4,155,763 | 5/1979 | Hasebe et al. | 430/469 |
| 4,522,917 | 6/1985 | Ichijima et al. | 430/564 |
| 5,017,454 | 5/1991 | Nakamine et al. | 430/203 |
| 5,156,940 | 10/1992 | Kok et al. | 430/230 |
| 5,474,879 | 12/1995 | Fitterman et al. | 430/483 |
| 5,618,652 | 4/1997 | Ueda et al. | 430/250 |

FOREIGN PATENT DOCUMENTS

| | | |
|---|---|---|
| 0 123 904 A1 | 11/1984 | European Pat. Off. |
| 62-178251 | 8/1987 | Japan. |
| 92/10789 | 6/1992 | WIPO. |

*Primary Examiner*—Hoa Van Le
*Attorney, Agent, or Firm*—J. Lanny Tucker

[57] ABSTRACT

A class of pyrazolidone compounds suitable for use as electron transfer agents in photographic development comprises pyrazolidones substituted in the 1-position by an aromatic group that is substituted in the ortho, meta or para position by —O—CO—R, wherein R is a monovalent organic group having up to 24 carbon atoms. This ester group is hydrolyzable in an alkaline developer solution, thereby deactivating the electron transfer agents after a period of time and reducing the contamination effect of seasoning into the developer solution. Photographic recording materials can be developed in reactive association with the electron transfer agent. The electron transfer agent can be present in the photographic recording materials, or in develper solutions.

3 Claims, 5 Drawing Sheets

AUXILIARY DEVELOPMENT AGENTS PHOTOGRAPHIC MATERIALS INCORPORATING THEM AND THE USE THEREOF

This is a divisional of recently allowed U.S. Ser. No. 08/970,640, filed Nov. 14, 1997.

FIELD OF THE INVENTION

This invention relates to new auxiliary developing agents, photographic materials in which they are incorporated and a process for the development of photographic materials in which they are used.

BACKGROUND OF THE INVENTION

Pyrazolidone electron transfer agents have been previously described for use as auxiliary developing agents in black-and-white and color photographic developers. It has been proposed to include these materials either in the developer solution or in the sensitized silver halide layer of a photographic film.

For example, U.S. Pat. No. 4,155,763 describes color developing solutions comprising an aromatic amine color developing agent and a 1-aryl-pyrazolidone having two substituents at the 4-position of the pyrazolidone. The advantages are said to include faster image dye formation and a more stable color developing solution.

The English language abstract of Japanese application 62/178251 describes a color developing solution comprising a para-phenylene color developing agent and an auxiliary developing agent including, inter alia, 1-phenyl pyrazolidone. Image formation is described as highly sensitive and forming excellent gradation.

WO 92/10789 describes the color development of an imagewise exposed photographic material in which the color development is carried out in the presence of one or a combination of black-and-white silver halide developing agents such as pyrazolidones, for example 1-(4-methoxyphenyl)-3-pyrazolidone, 1-(3,4-dimethoxyphenyl)-3-pyrazolidone and 1-phenyl-4-n-pentyl-pyrazolidone which provide acceptable sensitometric results with reduced variability.

When an electron transfer agent such as a pyrazolidone is incorporated in the sensitized layer, residual amounts can season into the developer solution and can affect other films which did not contain this material and which were not designed to be processed in its presence.

There is a need to solve this problem of the contamination of the developer solution by the presence of residual amounts of electron transfer agent when used for subsequent development.

SUMMARY OF THE INVENTION

According to the present invention there is provided a pyrazolidone compound suitable for use as an electron transfer agent in photographic development, the compound comprising a pyrazolidone substituted in the 1-position by an aromatic group, the aromatic group being substituted in the ortho, meta or para position by —O—CO—R wherein R is a monovalent organic group containing up to 24 carbon atoms.

This invention also provides a photographic recording material comprising a support and a photosensitive silver halide emulsion layer having in reactive association therewith an image dye-forming coupler compound and an electron transfer agent comprising the pyrazolidone compound described above.

Further, a photographic development process comprises developing an imagewise exposed photographic recording material in the presence of an electron transfer agent comprising the pyrazolidone described above.

Still further, this invention provides a photographic developer solution for photographic recording materials, the developer solution containing an electron transfer agent comprising the pyrazolidone described above.

The R group of the noted electron transfer agent preferably contains one or more aromatic rings. Particularly preferred compounds are those in which the R group comprises an aromatic ring which may be substituted, conveniently in the para position with a group that imparts solubility in alkaline developer solution, such as methane sulfonamido. The aromatic ring may also be substituted by an electron donor (which has the effect of increasing the rate of deactivation) for example, hydroxy, amino, hydroxyalkyl or the like. Alternatively the aromatic ring may be substituted by an electron withdrawing group such as nitro, sulfamoyl, carbamoyl, nitrile, and the like. Such groups have the effect of slowing the rate of deactivation of the electron transfer agent.

The pyrazolidone is preferably substituted in the 4-position by one or more organic groups ($R_2$ and $R_3$) each having up to 12 carbon atoms, preferably two alkyl groups which may be the same or different, each having up to 6 carbon atoms.

The problem noted above has been solved with the use of a novel class of compounds that can accelerate development, but are capable of becoming deactivated after a period of time in the developer solution. Thus, the compounds of the invention are useful as electron transfer agents but are deactivated after a period of time in the developer solution, thereby preventing or reducing contamination of the developer solution by the electron transfer agent leeched from a layer of photographic material.

DETAILED DESCRIPTION OF THE INVENTION

Preferred pyrazolidone electron transfer agents of the present invention can be represented by either of the following general formulae, which show alternative tautomeric forms:

wherein R is a monovalent organic group having up to 24 carbon atoms, preferably from 1 to 12 carbon atoms, and particularly from 1 to 6 carbon atoms, $R_1$ is hydrogen, $R_2$ and $R_3$ are independently hydrogen, substituted or unsubstituted alkyl having from 1 to 12 carbon atoms (such as hydroxyalkyl), carbamoyl, or substituted or unsubstituted aryl having from 6 to 10 carbon atoms, $R_4$ and $R_5$ are independently hydrogen, substituted or unsubstituted alkyl having from 1 to 8 carbon atoms, or substituted or unsubstituted aryl having from 6 to 10 carbon atoms, $R_6$ can be hydrogen, but if not hydrogen, it can be present in the ortho, meta or para positions of the benzene ring (with respect to the position attached to the nitrogen of the pyrazolidone), and be halogen, substituted or unsubstituted alkyl or alkoxy having from 1 to 8 carbon atoms, or sulfonamido, and when there is more than one $R_6$ substituent, they can be the same or different or can be taken together to form a carbocyclic or heterocyclic ring including a benzene ring.

Thus, n can be 0 or an integer of from 1 to 4.

When $R_2$ and $R_3$ are alkyl, it is preferred that they have 1 to 6 carbon atoms and more preferably, 1 to 3 carbon atoms. When $R_2$ and $R_3$ are each aryl, they are preferably phenyl. $R_4$ and $R_5$ are preferably hydrogen.

When $R_6$ is sulfonamido, it can be methanesulfonamido, ethanesulfonamido or toluenesulfonamido.

The electron transfer agent which is substituted in the aromatic ring with the —OCOR group can be any of those disclosed in EP-A-0 347 848A.

It is preferred that the —OCOR group be attached to the ortho, or para positions (with respect to the position attached to the nitrogen atom of the pyrazolidone ring).

The amount of electron transfer agent employed in this invention can be any concentration which is effective for the intended purpose. Suitable amounts are typically in the range from about 0.04 to about 8 mmol/m², preferably from about 0.2 to about 1.8 mmol/m², and more preferably from about 0.5 to about 1.5 mmol/m², of photographic recording material.

Especially preferred compounds ("ETA") within the two tautomeric structural formulae noted above are represented in the following Table.

| ETA | $R_2$ | $R_3$ | $R_6$ |
|---|---|---|---|
| 1 | —H | —H | —H |
| 2 | —CH$_3$ | —H | —H |
| 3 | —CH(CH$_3$)$_2$ | —H | —H |
| 4 | —CH$_3$ | —CH$_2$OH | —H |
| 5 | —H | —H | p-CH$_3$ |
| 6 | —H | —H | p-OCH$_3$ |
| 7 | —CH$_3$ | —CH$_2$OH | p-CH$_3$ |
| 8 | —CH$_3$ | —CH$_2$OH | p-OCH$_3$ |

R is preferably an aromatic ring that can be substituted by a group that imparts solubility in alkaline developer solution, for example sulfonamido or methanesulfonamido, and optionally also by an electron donor (which has the effect of increasing the rate of deactivation) such as hydroxy, amino, hydroxyalkyl and the like.

Alternatively, the aromatic ring may be substituted with an electron withdrawing group such as nitro, sulfamoyl, carbamoyl, nitrile and the like which have the effect of slowing the rate of deactivation.

The electron transfer agents of this invention may be incorporated into black-and-white papers or films as auxiliary developing agents, or into color negative papers or films where they may be used to lower process sensitivity, or they may be used to accelerate development in all of the elements noted above. These types of papers and films are well known in the art, as described, for example, in Research Disclosure, publication 38957, September 1996.

Preferably there is incorporated into the developer solution used in the development process of this invention, a catalyst such as hydroxylamine, in an effective amount for the decomposition of the electron transfer agent. Thus, the catalyst can be generally present in the developer solution in an amount of from about 0.1 to about 20 g/l, preferably at from about 2 to about 5 g/l.

In carrying out the development process, it is preferred that the electron transfer agent be incorporated into a layer of the photographic recording material. However, it is possible to provide the electron transfer agent in the developer solution itself. But this is not preferred because contamination of the developer solution with residual amounts of electron transfer agent is more likely to occur in such embodiments. When incorporated into the developer solution, the electron transfer agent is generally present in an amount of from about $1 \times 10^{-4}$ to about $5 \times 10^{-3}$ molar, and preferably from about $3 \times 10^{-4}$ to about $1 \times 10^{-3}$ molar.

The invention is illustrated by the following Examples.

EXAMPLE 1

Synthesis of ETA 1

To a solution of p-nitrophenol (13.9 g, 0.1 mol) in dry tetrahydrofuran (200 ml) was added triethylamine (11.0 g, 0.11 mol) at room temperature with stirring. The reaction mixture was cooled to about 10° C. and benzoyl chloride (14.5 g, 0.103 mol) was added dropwise to the above mixture at such a rate that the temperature did not rise above 15° C. After the addition was completed, the mixture was stirred at room temperature for 20 hours before pouring into a mixture of ice/water (1:1) and concentrated hydrochloric acid with rapid stirring. The white precipitate was collected by filtration and washed with water (1:1) under suction. After drying under vacuum over P$_2$O$_5$ at 45° C., a white solid was obtained as the required intermediate (1). Yield, 24.2 g (99.5%).

This compound was used in the next stage of the synthesis without further purification.

A solution of intermediate (1) (5.0 g, 20.5 mmol) in dry tetrahydrofuran (250 ml) was hydrogenated over 10% palladium on charcoal (0.5 g) under 32 atmospheres of hydrogen. The hydrogenation was over 2.5 hours at room temperature. After removal of the catalyst, the solvent was rotary evaporated to dryness to give the required aniline (2) as an off-white solid. Yield 4.4 g (100%). Aniline (2) was used in the next stage of the synthesis without further purification.

To a suspension of the aniline (2) (4.28 g, 20 mmol) in a mixture of concentrated hydrochloric acid (23 ml) and water (8 ml) was added dropwise in an ice-cold solution of sodium nitrite (1.5 g, 21.8 mmol) in water (4.5 ml) at 0° C. with rapid stirring. The addition was carried out over a period of 15 minutes and the mixture was then stirred at 0° C. for a further 15 minutes. This mixture was poured into a solution of tin (II) chloride (16.8 g, 88.7 mmol) in a mixture of concentrated hydrochloric acid (180 ml) at room temperature with stirring. After stirring for about one hour, the precipitate was collected by filtration under suction. The crude material was triturated with acetonitrile (80 ml) filtered and dried under vacuum to give the required hydrazine hydrochloride (3). Yield 3.54 g, (67%). The hydrazine hydrochloride (3) was used in the preparation of ETA 1 without further purification.

To a suspension of the hydrazine hydrochloride (3) in dry pyridine (10 ml) was added dropwise 3-chloropivaloyl chloride (0.59 g, 3.78 mmol), at 5° C., over a period of 10 minutes. The mixture was stirred at about 5° C. for a further one hour and then at room temperature for 22 hours. After pouring into a rapidly stirred mixture of ice/water (150 ml) and concentrated hydrochloric acid (12 ml) a pale yellow precipitate was formed. The solid was collected by filtration under suction and the damp solid dissolved in ethyl acetate (150 ml). The organic solution was washed with water (100 ml) and then brine (100 ml). After drying over magnesium sulfate, the solvent was removed under reduced pressure and the resultant solid triturated with diethyl ether (50 ml). The solid was collected by filtration under suction and then dried in vacuum. The required product, ETA 1, was obtained as a cream colored solid. Yield, 0.92 g (79%).

$C_{18}H_{18}N_2O_3$ calculated: C, 69.66; H, 5.85; N, 9.03% found: C, 69.68; H, 5.75; N, 8.97%

This synthetic route is illustrated as follows:

Use of ETA 1 as an Electron Transfer Agent in a Color Development Process

A color negative developer composition shown in Table 1 was made with and without hydroxylamine (HAS).

TABLE 1

| potassium carbonate (anhydrous) | 37.5 g/l |
| sodium sulfite (anhydrous) | 4.25 g/l |
| potassium iodide | 1.2 mg/l |
| sodium bromide | 1.3 g/l |
| hydroxylamine sulfate | 2.0 g/l |
| anti-calcium sequestering agent | 6.5 ml/l |
| color developing agent | 4.5 g/l |
| pH | 10.00 |

The anti-calcium sequestering agent was a 40% w/w aqueous solution of the pentasodium salt of diethylene triamine pentaacetic acid and the color developing agent was 4-amino-3-methyl-N-ethyl-N-(hydroxyethyl) aniline sulfate.

An electron transfer agent of the structure shown as ETA 1 was examined as a development accelerator for a single layer color negative material comprising a silver bromoiodide emulsion (0.9 g/m$^2$) and a cyan image forming coupler (0.6 g/m$^2$). ETA 1 (0.15 g/l) was dissolved in the developer shown in Table 1 but without any hydroxylamine sulfate (HAS) present.

Figure 1:
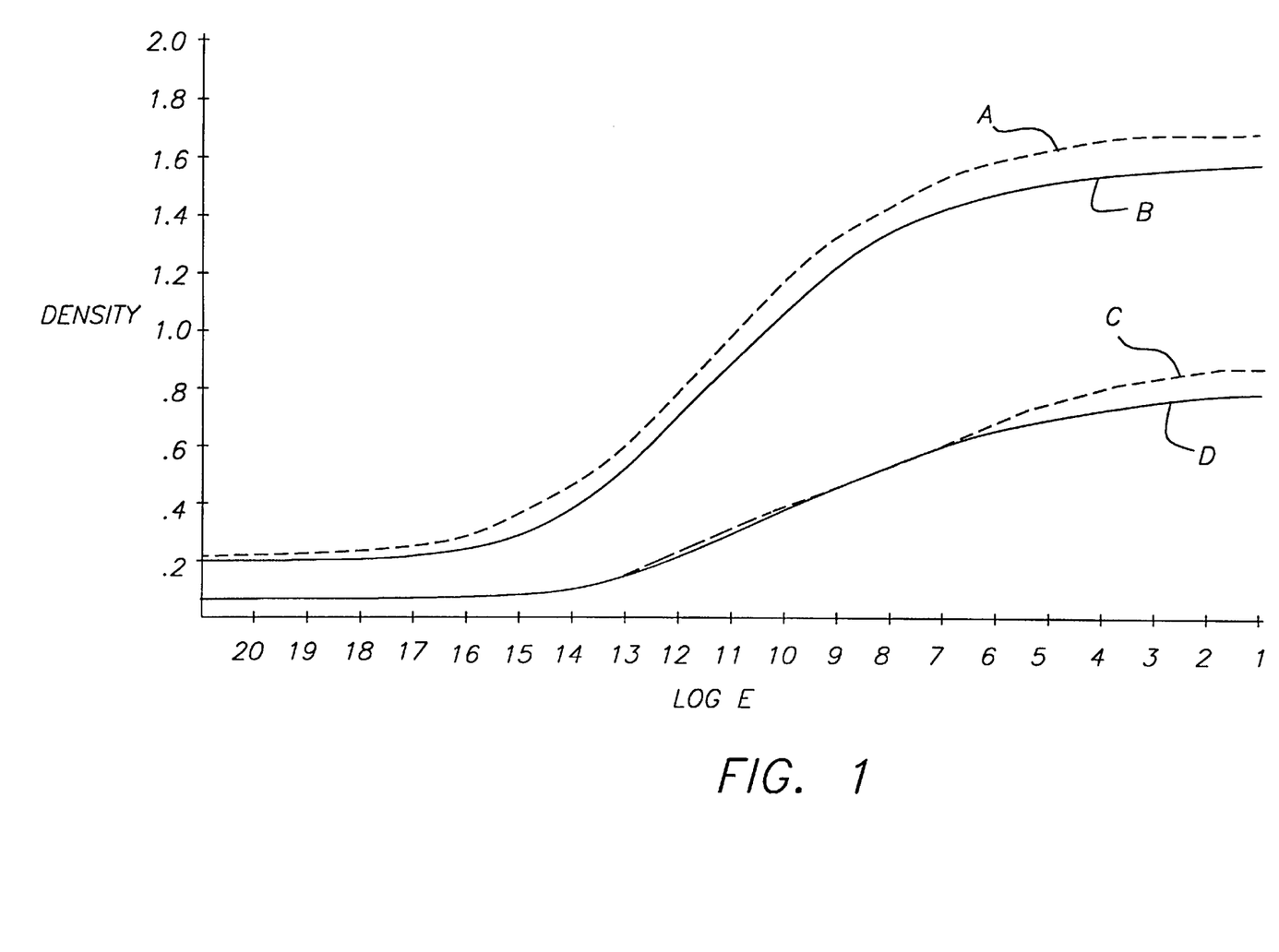
FIGS. 1–4 are graphical plots in which density of the image dye is plotted against the log of the exposure in the case of the development of color negative films. The plots show the results with and without an electron transfer agent, and with and without hydroxylamine, in the developer solution.

The result shown in FIG. 1 was obtained. Curves A and B represent data from 2.5 minute development, with and without ETA 1, respectively. Curves C and D represent data from 1 minute development, with and without ETA 1, respectively. It can be seen that there is a small acceleration in development after 2.5 minutes, but very little after 1 minute.

Figure 2:
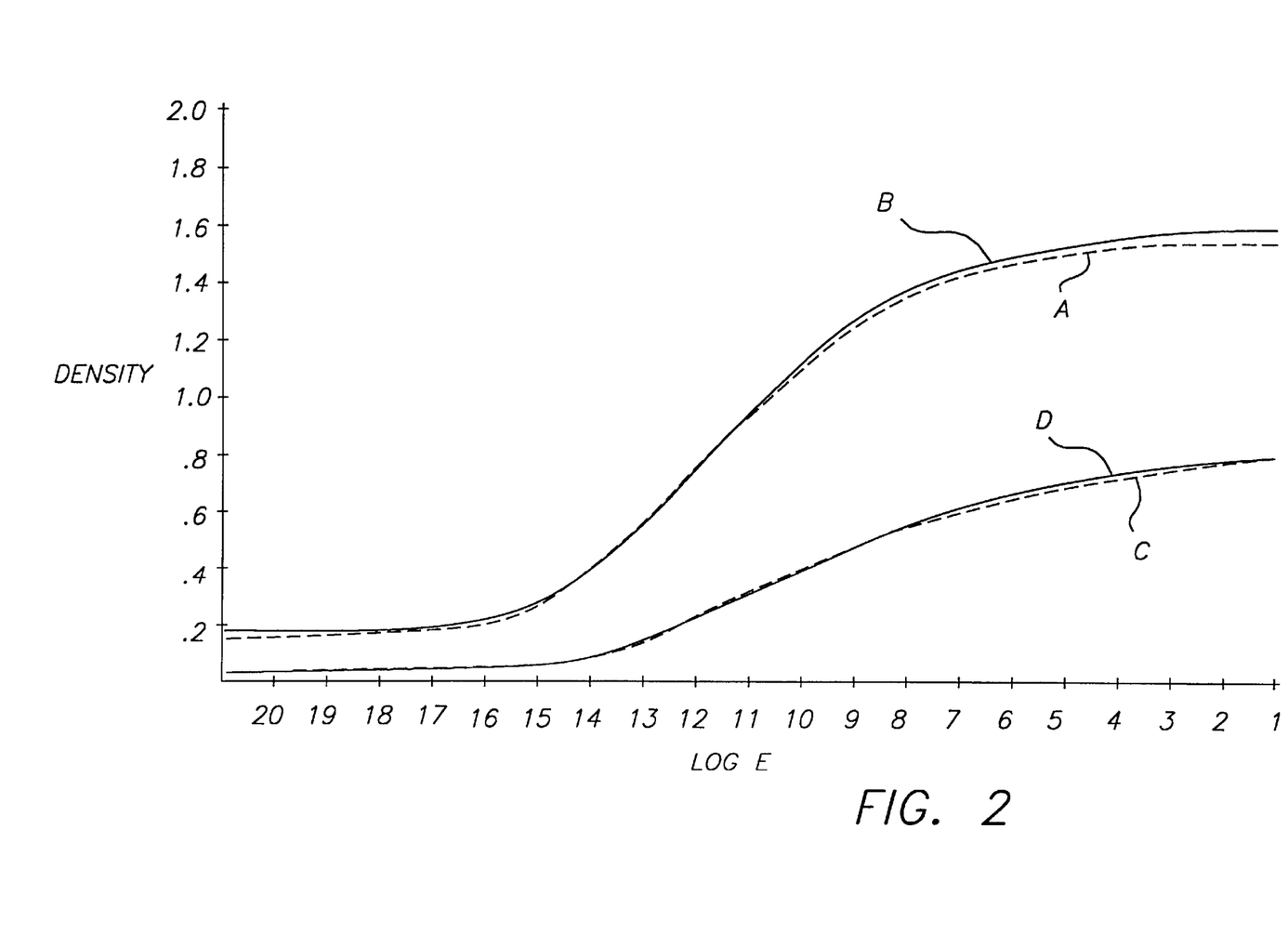

When hydroxylamine (HAS) was included in the developer solution, the small amount of acceleration disappeared as can be seen from FIG. 2. Curves A, B, C and D in FIG. 2 represent the same conditions as for FIG. 1. The first film strips were processed 10 minutes after ETA 1 was added to the developer solution. It is apparent that within this time, ETA 1 had degraded and was no longer acting as a development accelerator. It is also clear that the loss of ETA 1 is accelerated by the presence of HAS in the developer.

EXAMPLE 2

Synthesis of ETA 2.

To a solution of ethyl 4-aminobenzoate (16.5 g, 0.1 mol) and N,N-dimethylaniline (13.3 g, 0.11 mol) in dry tetrahydrofuran (100 ml) was added dropwise methane sulfonyl chloride (12.6 g, 0.11 mol) at room temperature with stirring. The mixture was then refluxed for 20 hours. After cooling to room temperature the mixture was poured into ice/water (1:1) and concentrated hydrochloric acid (20 ml) with rapid stirring. The resultant solid (4) was collected and washed with water by filtration under suction. The damp solid was dissolved in a mixture of tetrahydrofuran (90 ml) and ethanol (80 ml). A solution of sodium hydroxide (12 g, 0.3 mol) in water (80 ml) was then added to the above solution and refluxed for 24 hours. After cooling to room temperature, the reaction mixture was poured into a mixture of ice/water (1:1) and concentrated hydrochloric acid (50 ml) with rapid stirring. The white solid was collected by filtration under suction and then dried at 40° C. over $P_2O_5$ to give the required product (5). Yield 19.5 g, (91%).

This compound was used in the next stage of the synthesis without further purification.

A suspension of the product (5) (14.3 g, 66.5 mmol) in a mixture of thionyl chloride (11.5 g, 96.6 mmol) and ethyl acetate (60 ml) was refluxed for 24 hours. After cooling to room temperature and then in an ice/water bath for a further 15 minutes, a white solid was formed and was collected and washed with diethyl ether by filtration under suction. The crude product was dissolved in dry tetrahydrofuran (60 ml) and added dropwise to a mixture of p-nitrophenol (9.23 g, 66.4 mmol) and triethylamine (7.3 g, 72 mmol) in dry tetrahydrofuran (100 ml) at 5° C. with stirring over a period of 30 minutes. The reaction mixture was stirred at room temperature for about 24 hours and then poured into a mixture of ice/water (1.51) and concentrated hydrochloric acid with rapid stirring. The resultant solid was collected and washed with water by filtration under suction. The product (6) was obtained as a creamy white solid after drying under vacuum over $P_2O_5$ at 40° C. Yield 17.8 g (79%).

Product (6) (17.5 g, 52.1 mmol) in tetrahydrofuran (500 ml) was hydrogenated over 10% palladium on charcoal (1.7 g) at 35° C. under 34 atmospheres of hydrogen for 24 hours. After removal of the catalyst by filtration, the filtrate was treated with hydrochloric acid gas with cooling in an ice/water bath. A white precipitate was formed and was collected and washed with cold tetrahydrofuran under suction. After drying under vacuum, the amine hydrochloride (7) was isolated as a white solid. Yield 17.5 g (98%).

To a suspension of the finely powdered amine hydrochloride (7) (1 g, 2.92 mmol) in a mixture of concentrated hydrochloric acid (10 ml) and water (3 ml) was added dropwise an ice-cold solution of sodium nitrite (0.25 g, 3.6 mmol) in water (1 ml) at 5° C. with rapid stirring. After the addition was completed, the mixture was stirred at about 10° C. for a further 10 minutes after which a complete solution was observed. The above solution was added dropwise to a solution of tin (II) chloride (2.3 g, 12.3 mmol) in a mixture of concentrated hydrochloric acid (15 ml) and water (35 ml) at about 10° C. with rapid stirring. A white precipitate separated and was collected by filtration under suction. The solid was washed with cold hydrochloric acid (3 Normal) dried under vacuum over $P_2O_5$ at 40° C. to give an off-white solid (1 g). This solid was triturated with tetrahydrofuran (35 ml) filtered and dried under vacuum to give the required hydrazine hydrochloride (8) as a tan colored solid. Yield 0.85 g (81%).

To a suspension of the hydrazine hydrochloride (8) (0.85 g, 2.38 mmol) in dry pyridine (10 ml) was added dropwise 2-chloropivaloyl chloride (0.38 g, 2.45 mmol) with stirring. The reaction mixture was stirred at 5° C. for a further 2 hours and then at room temperature for 22 hours. After pouring into a rapidly stirred mixture of concentrated hydrochloric acid (12 ml) and ice/water (120 ml), a precipitate was formed and was collected and washed with water by filtration under suction. A light brown solid (0.9 g) was obtained after drying under vacuum over $P_2O_5$. The crude product was purified by column chromatography (160 g of silica gel eluted with ethyl acetate) and the fractions containing the required product were combined and concentrated under reduced pressure. The residual gum was dissolved in a minimum of tetrahydrofuran and added dropwise to rapidly stirred petrol (60 to 80° C.) (200 ml). The precipitate was collected by filtration under suction and then dried under vacuum to give the required product (ETA 2) as a peach colored solid. Yield 0.77 g (80%).

1H-NMR (DMSO-d6):1.05 (s, 6H), 3.15 (s,3H), 3.7(s, 2H), 7.05 (d,2H), 7.15 (d,2H), 7.35 (d,2H), 8.05 (d,2H), 10.15(s,1H), and 10.4 (s, 1H). M/z:403.

Figure 3:
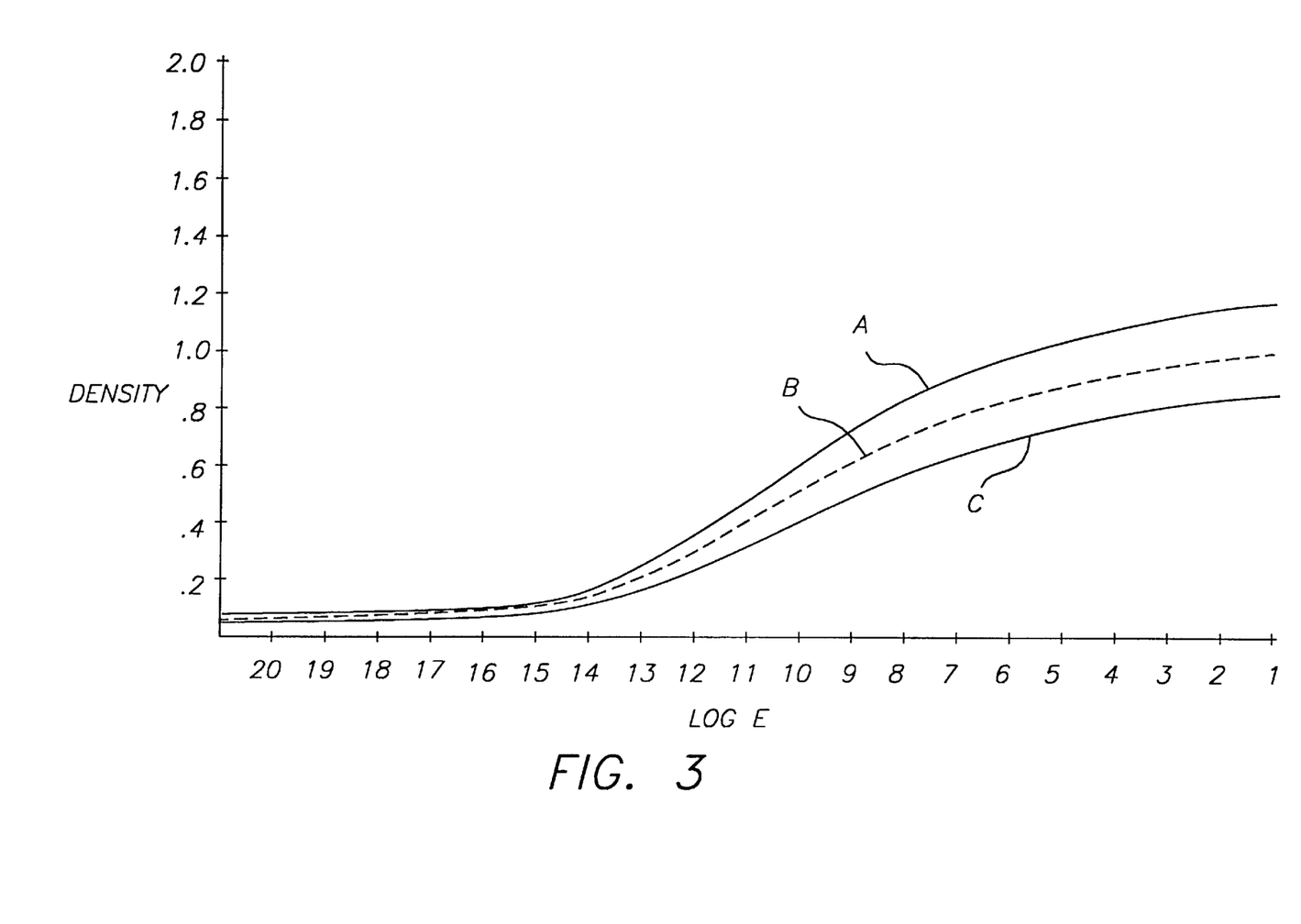

This synthetic route is illustrated as follows:

Use of Compound ETA 2 as an a Electron Transfer Agent in a Color Development Process ETA 2 was evaluated in the same element described in Example 1. The result is shown in FIG. 3 for 1 minute development time in the developer shown in Table 1 with varying amounts of ETA 2, and without hydroxylamine present. Curve A represents 0.2 g/l ETA 2, Curve B represents 0.1 g/l ETA 2, and Curve C represents no ETA 2. Here it can be seen that there is a significant acceleration of development caused by ETA 2.

Figure 4:
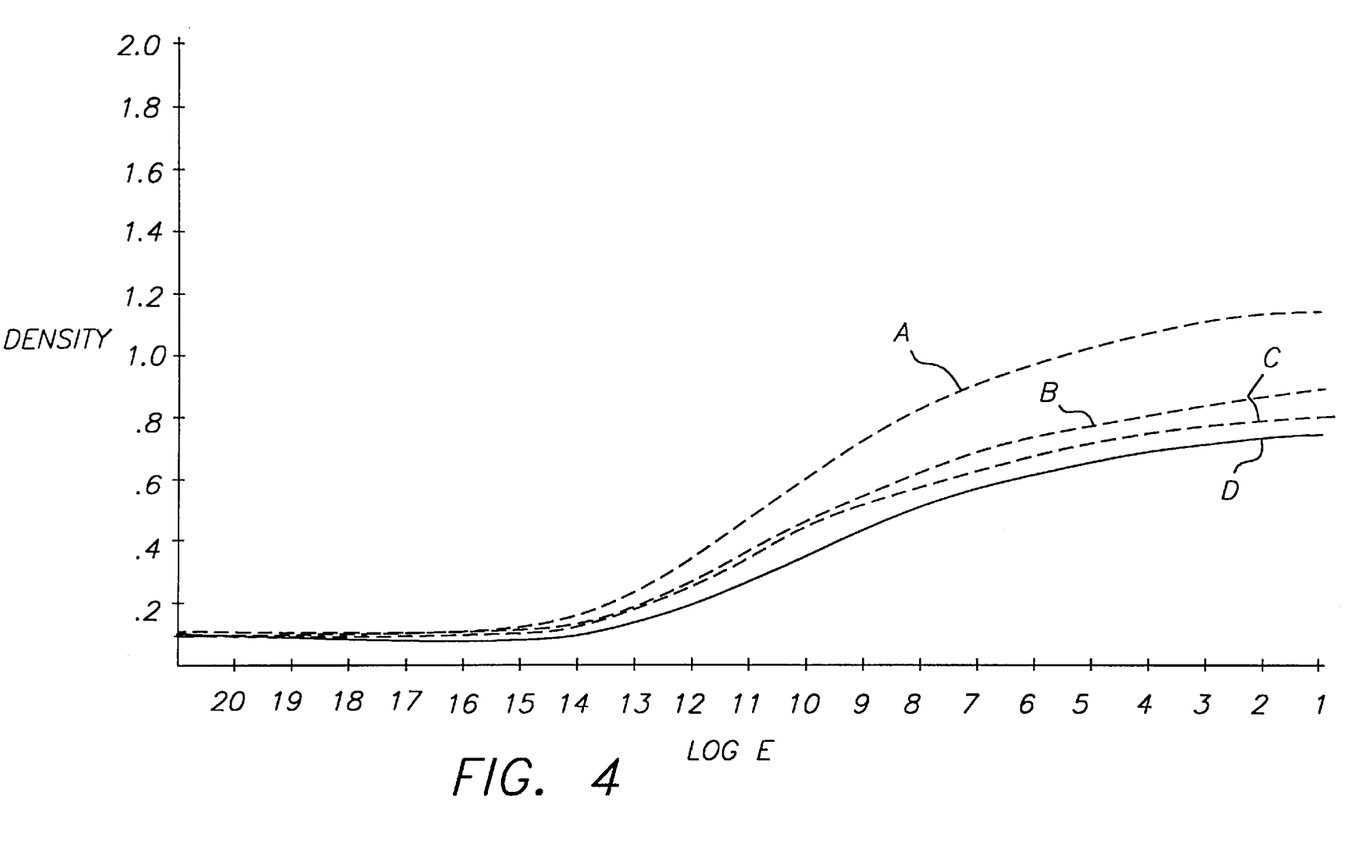

Hydroxylamine was added to the developer solution and film strips were processed as soon as possible afterwards and it can be seen from FIG. 4 that in about 1.5 minutes there was a significant reduction in the amount of development acceleration. Curve A represents 0.2 g/l of ETA 2 and no HAS. Curve B represents 0.2 g/l ETA 2, and 1 minute development after addition of HAS (2 g/l, 1 minute, 22 seconds later). Curve C represents 0.2 g/l ETA 2, and 1 minute development after addition of HAS (2 g/l, 1 hour, 16 minutes after addition). Curve D represents the use of HAS (2 g/l) and no ETA 2. A developer without either ETA 2 and HAS gave the same results shown as Curve C. Film strips were processed over a period of time and the activity of the compound ETA 2 gradually diminished until it was almost equivalent to the control without any ETA 2.

These results demonstrate that the electron transfer agent ETA 2 is a development accelerator and that in the presence of hydroxylamine, it loses its accelerating ability within a period of several minutes.

EXAMPLE 3

Figure 5:
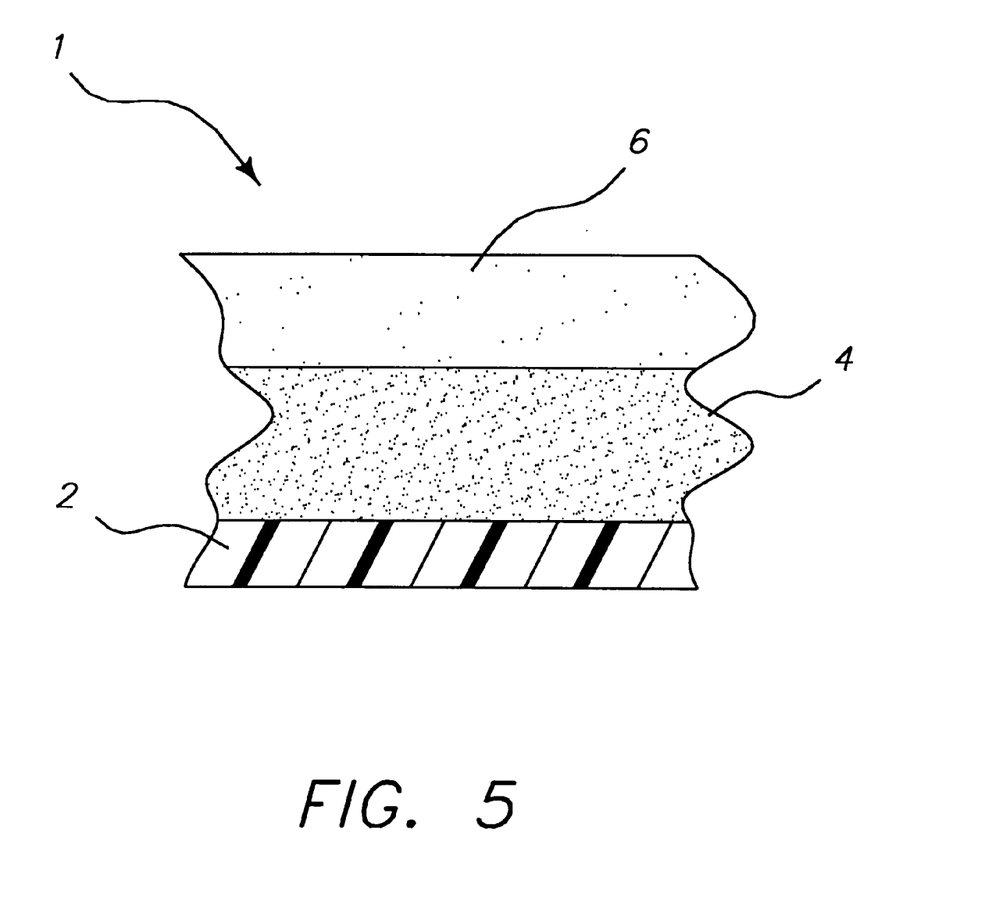
FIG. 5 is a schematic representation of a photographic material in which an electron transfer agent is incorporated into a layer.

Referring to FIG. 5, a photographic recording material 1 comprises antihalation support 2, emulsion layer 4 containing a color coupler, silver halide and ETA 2, and gelatin overcoat layer 6.

The coupler was a cyan coupler having the structure labeled C1 below, coated at 0.6 g/m$^2$. The silver halide was a 400 speed silver bromoiodide (4% iodide) T-grain emulsion coated at 0.9 g/m$^2$. Gelatin was coated at 2.7 g/m$^2$ in emulsion layer 4 and at 1.0 g/m$^2$ in overcoat layer 6. ETA 2 was coated at.0.1 g/m$^2$.

Coupler C1

ETA 2 was stable in the coating until the element was processed in the developer solution shown in Table 1 above. Development of the silver bromoiodide emulsion commenced and was accelerated by ETA 2. In about one minute, most ETA 2 had diffused out of the layer and into the developer solution, and in the next few minutes ETA 2 was deactivated by the action of the hydroxylamine in the developer solution.

In order for the effective working of the invention, the rate of deactivation of the ETA must not be so high as to prevent it acting as a development accelerator which will occur primarily during the first minute of the development. It is clear that compound ETA 2 has achieved this objective since it lost about 70% of its accelerating ability within one minute and 22 seconds. Thus, during this period and primarily during the first minute before the ETA diffuses out of the layer, it is able to act as a development accelerator.

It is also clear that a range of ETA types based on 1-phenyl-3-pyrazolidone with a hydrolyzable ester group on the phenyl ring, but with different substituents than those in ETA 2 (to either increase or decrease the accelerating ability or to increase or decrease its rate of deactivation) can be employed in this invention.

The invention has been described in detail with particular reference to certain preferred embodiments thereof, but it will be understood that variations and modifications can be effected within the spirit and scope of the invention.

We claim:

1. A photographic developer solution for photographic recording materials, said developer solution containing an electron transfer agent comprising a pyrazolidone substituted in the 1-position by an aromatic group, said aromatic group being substituted in the ortho, meta orpara position by a hydrolyzable —O—CO—R group wherein R is a monovalent organic group containing up to 24 carbon atoms.

2. The developer solution of claim 1 wherein said electron transfer agent is present in an amount of from about $1 \times 10^{-4}$ to about $5 \times 10^{-3}$ molar.

3. The developer solution of claim 1 further comprising a catalyst for deactivating said electron transfer agent.

* * * * *